United States Patent [19]
Mundt

[11] Patent Number: 5,654,796
[45] Date of Patent: Aug. 5, 1997

[54] APPARATUS AND METHOD FOR MAPPING PLASMA CHARACTERISTICS

[75] Inventor: Randall S. Mundt, Pleasanton, Calif.

[73] Assignee: LAM Research Corporation, Fremont, Calif.

[21] Appl. No.: 577,513

[22] Filed: Dec. 22, 1995

[51] Int. Cl.$^6$ .................................................. G01N 21/62
[52] U.S. Cl. ............................................................. 356/316
[58] Field of Search .................................... 356/311, 316

[56] References Cited

U.S. PATENT DOCUMENTS

| | | |
|---|---|---|
| 3,752,915 | 8/1973 | Parker et al. . |
| 3,817,622 | 6/1974 | Billman et al. . |
| 3,833,851 | 9/1974 | Jobes, Jr. et al. . |
| 4,541,718 | 9/1985 | Osada et al. ........................ 356/316 |
| 4,602,981 | 7/1986 | Chen et al. . |
| 4,675,072 | 6/1987 | Bennett et al. . |
| 4,682,605 | 7/1987 | Hoffman . |
| 4,687,344 | 8/1987 | Lillquist . |
| 4,707,147 | 11/1987 | Aoki et al. . |
| 4,846,920 | 7/1989 | Keller et al. . |
| 4,902,139 | 2/1990 | Adiutori . |
| 5,045,149 | 9/1991 | Nulty . |
| 5,082,517 | 1/1992 | Moslehi . |
| 5,103,182 | 4/1992 | Moslehi . |
| 5,147,520 | 9/1992 | Bobbio . |
| 5,167,748 | 12/1992 | Hall . |
| 5,235,465 | 8/1993 | Hayashi .............................. 359/659 |
| 5,359,681 | 10/1994 | Jorgenson et al. .................. 356/320 |
| 5,444,241 | 8/1995 | Del Grande et al. . |

FOREIGN PATENT DOCUMENTS

| | | | |
|---|---|---|---|
| 57-207849 | 12/1982 | Japan ................................ 356/316 |
| 57-207850 | 12/1982 | Japan ................................ 356/316 |
| 58-28714 | 2/1983 | Japan ................................ 356/316 |
| 2-201141 | 8/1990 | Japan ................................ 356/316 |

*Primary Examiner*—F. L. Evans
*Attorney, Agent, or Firm*—Burns, Doane, Swecker & Mathis, L.L.P.

[57] ABSTRACT

An apparatus and method for mapping characteristics of a volume of plasma in a plasma reaction chamber uses a photosensitive detector, a scanner that scans the volume, and a light directing element that directs light emissions from the volume scanned by the scanner to the photosensitive detector. The photosensitive detector generates a signal corresponding to a detected amount of the light emissions from the volume and the signal is processed to estimate one or more characteristics of the volume.

20 Claims, 1 Drawing Sheet

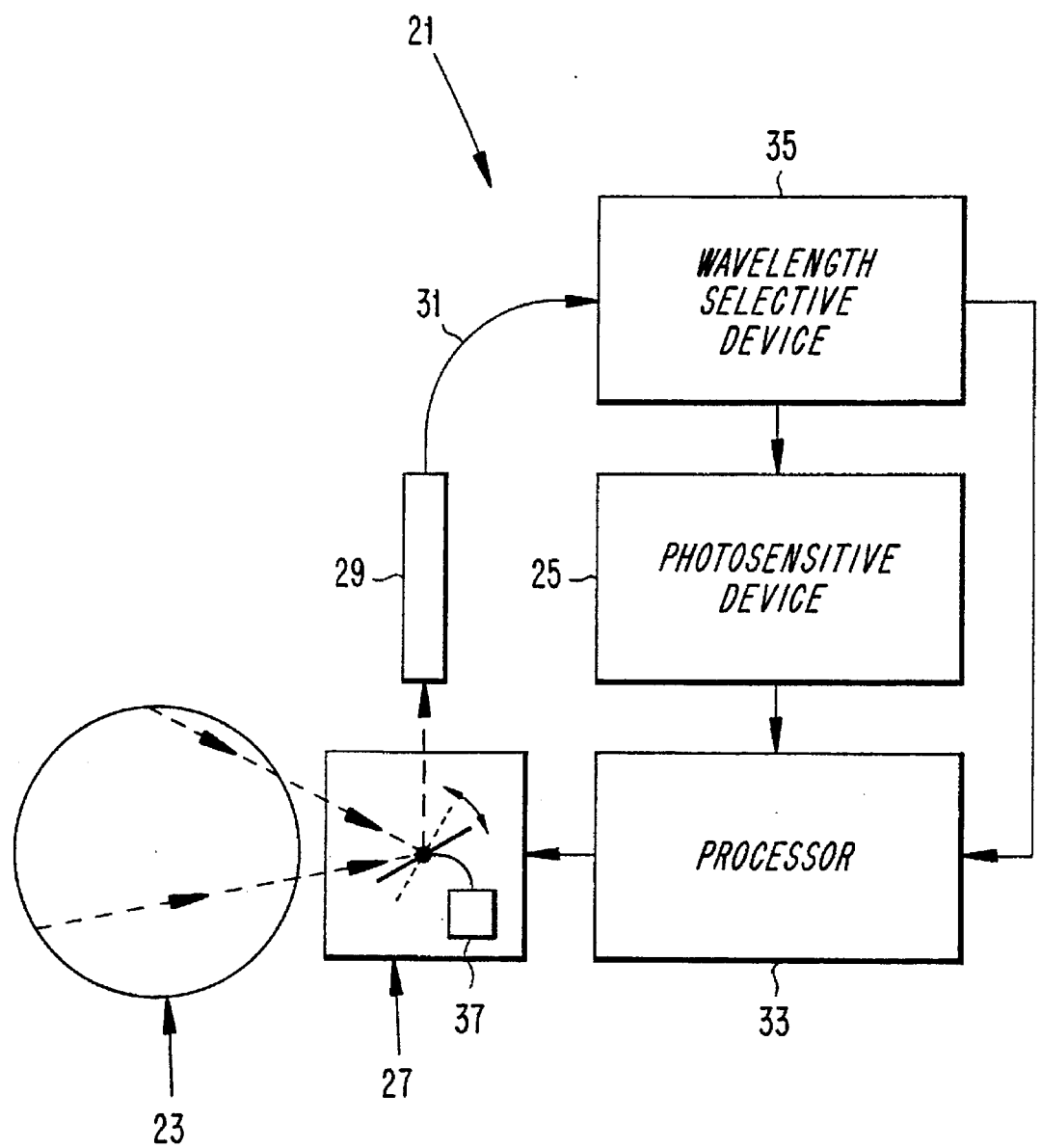

APPARATUS AND METHOD FOR MAPPING PLASMA CHARACTERISTICS

FIELD OF THE INVENTION

The present invention relates to measurement of plasma characteristics and, more particularly, to mapping of localized characteristics of a plasma.

BACKGROUND AND SUMMARY OF THE INVENTION

Plasma etching operations are common in the manufacture of articles such as integrated circuits. The performance of the plasma etch operation is highly dependent on the density and uniformity of the plasma. In the past, optical emission methods have been used to monitor the density of the plasma. For example, the ratio of emissions from two different species has been used as an estimate of the relative abundance of ionic or excited species.

Typical optical emission spectroscopy measurements are made using light from a large volume of the plasma discharge. The measurement of the large volume thus represents an average concentration or integrated concentrations within the observed volume. Information concerning localized density or concentration measurements cannot be determined with such measurement techniques. U.S. Pat. No. 4,615,761 provides an example of a method and apparatus wherein a sample is only taken from a single location in the plasma.

In view of the deficiencies and disadvantages of the prior art plasma density measurement techniques, it would be desirable to provide an apparatus and method for acquiring spatially resolved density and concentration information concerning a plasma.

In accordance with one aspect of the invention, an apparatus for measuring plasma characteristics at various locations in a plasma in a plasma reaction chamber is provided. The apparatus includes a photosensitive detector, and a scanner that receives light emissions from different points in a volume of plasma in a plasma reaction chamber. The apparatus further includes a light directing element that directs light emissions from the volume scanned by the scanner to the photosensitive detector, the photosensitive detector generating signals corresponding to detected amounts of the light from the volume at the different points. The apparatus also includes a processor wherein the signals are analyzed and converted to data representative of characteristics of the plasma at the different points.

In accordance with another aspect of the present invention, a method for mapping characteristics at different locations in a volume of plasma in a plasma reaction chamber is disclosed. According to the method, a volume of plasma in a plasma reaction chamber is scanned to obtain light emission samples from different points in the volume of plasma. Light emissions from the scanned volume are directed to a photosensitive detector. One or more signals corresponding to amounts of light emissions detected by the photosensitive detector are generated. The signals are processed to estimate one or more characteristics of the plasma at the different points.

BRIEF DESCRIPTION OF THE DRAWING

Features and advantages of the present invention are described in the following detailed description in conjunction with the drawing which schematically shows an apparatus for mapping characteristics of a plasma according to an embodiment of the present invention.

DETAILED DESCRIPTION OF THE INVENTION

An apparatus 21 for mapping characteristics of a volume 23 of plasma in a plasma reaction chamber is shown in the drawing. The volume 23 can be in a chamber of a plasma etching apparatus or other plasma generating equipment used for deposition, resist stripping, or the like. The chamber is preferably provided with a small window or other optical access port to permit light transmission for observation of the volume.

The apparatus 21 preferably includes a photosensitive detector 25 and a scanning arrangement such as a pivotable or rotatable mirror 27 or a solid state beam steering mechanism for scanning the volume 23. Light emissions in a path through the volume 23 scanned by the scanning arrangement are directed to the photosensitive detector 25 by a light directing arrangement, preferably an optical lens train 29 including a fiber optic connection 31, for providing a highly collimated collection beam. The optical lens train 29 preferably includes an input lens having a diameter or aperture chosen based on a desired spatial resolution of the characteristics of the volume sought to be mapped. The photosensitive detector 25 generates a signal corresponding to a detected amount of the light from the volume 23 and a processor device 33 such as a computer analyzes or processes the signal to estimate one or more characteristics of the volume 23, such as plasma density, and/or chemical species of the plasma.

The photosensitive detector 25 preferably includes a photomultiplier tube and an associated high voltage power supply. However, the photosensitive detector may include other photosensitive devices such as a photodiode, or a charge coupled device. A photomultiplier tube is preferred largely because of the high sensitivity and speed of such a device which provides the ability to perform rapid scans of the plasma. The photosensitive detector 25 may be provided in the form of an array of photosensitive detectors. In such an embodiment, different ones of the photosensitive detectors 25 are preferably arranged to detect different ranges of wavelengths of the light from the volume 23. The different ones of the photosensitive detectors 25 preferably generate signals corresponding to detected amounts of the light from the volume 23 at the different ranges of wavelengths, which signals are thereupon processed by the processor to estimate characteristics of the volume. This arrangement is particularly useful for generating data on the chemical species comprising the plasma.

Instead of, or in addition to, an array of photosensitive detectors 25, the apparatus 21 may include a wavelength selective element 35 for preventing light from the volume 23 that is outside of a predetermined range of wavelengths from being detected by the photosensitive detector. The wavelength selective element 35 may be in the form of, for example, an optical filter, a rotating filter wheel, a spectrometer, or the like. A spectrometer is particularly preferred, however, because of the high spectral resolution obtainable which allows for the selection of the emission from specific chemical species. The processor 33 may be used to generate signals for the control of which wavelengths are transmitted by the wavelength selective element 35.

If a mirror 27 that may be turned, i.e., pivoted or rotated, is used as the scanning device, the mirror is preferably turned by a motor 37. The motor 37 may be arranged to continuously rotate the mirror 27 to repeatedly scan the volume 23.

The processor 33 preferably keeps track of the angle through which the beam steering device such as the mirror 27 scans the volume 23. The processor 33 preferably interacts with the motor 37 so that the processor controls angle of the volume 23 that is scanned at any given time.

A method for mapping characteristics of the volume 23 according to the present invention includes the step of scanning the volume, e.g., by means of a mirror 27 or solid state device that scans the volume of a reaction chamber apparatus through a window or other port in the chamber walls of the plasma etch apparatus. The method also includes the step of directing light from the scanned volume 23 to a photosensitive detector 25 by suitable means such as an optical lens train. One or more signals corresponding to the amount of light detected by the photosensitive detector 25 are generated and processed by a processor 33 to estimate one or more characteristics of the scanned volume.

To assist in estimating certain specific characteristics of the volume 23, light outside of a predetermined wavelength is, according to an embodiment of the invention, prevented from being detected by the photosensitive detector 25. In addition, or in the alternative, the photosensitive detector 25 may, according to another embodiment, include an array of photosensitive detectors, with different ones of the array of photosensitive detectors detecting different wavelengths of the light directed from the scanned volume 23. The photosensitive detectors comprising the array of photosensitive detectors preferably generate one or more signals corresponding to an amount of light at the different wavelengths detected by the different ones of the photosensitive detectors, which signals are then processed by the processor 33 to estimate characteristics of the volume.

According to another embodiment in addition or in the alternative to the foregoing embodiments, the volume 23 may be scanned a plurality of times by the scanning arrangement, such as by continuously rotating the mirror 27. Light outside of a first predetermined range of wavelengths is preferably prevented from being detected by the photosensitive detector 25 by the wavelength selective element 35 during a first one or more scans of the volume and, subsequently, the wavelength selective element prevents light outside of a second predetermined range of wavelengths from being detected by the photosensitive detector during a second one or more scans of the volume.

The signal generated by the photosensitive detector 25 represents the integral of the emission for the plasma along the light path through the plasma scanned by the scanning device 27. The amplitude of the signal generated by the photosensitive detector 25 will vary depending upon the length of the light path through the plasma as the beam steering mechanism such as the mirror 27 is turned. The processor 33 processes the signals from the photosensitive detector 25 by means of one of the many well-known methods for converting line integral measurements of an area or volume source into an estimation of local density or emission. For instance, in the case of a circular chamber, one such method utilizes a so-called Able transform. The Able transform, however, assumes radial symmetry, with respect to the source, and that measurements are made at equal spacings parallel to a diameter of the source. Since the apparatus 21 according to the present invention generates an angular scan rather than a linear scan, the Able transform or other method is modified as necessary, such as to account for the changes in signal amplitude due to, for example, changes in the length of the cord through the plasma that is scanned.

The present invention permits assembly of the apparatus 21 at low cost, as the component parts are generally inexpensive and simple to combine. The apparatus is flexible, and may be simply configured to provide estimations of plasma density, i.e., power distribution, reactant chemical species, and byproduct chemical species. The use of an angular scanning device such as a pivotable mirror 27 permits the apparatus 21 to be easily integrated with existing plasma chambers, which require only small windows or optical access ports to permit plasma mapping according to the present invention.

While this invention has been illustrated and described in accordance with a preferred embodiment, it is recognized that variations and changes may be made therein without departing from the invention as set forth in the claims.

What is claimed is:

1. An apparatus for measuring plasma characteristics at various locations in a plasma in a plasma reaction chamber, comprising:

a photosensitive detector;

a scanner that receives light emissions from along different paths in a volume of plasma in a plasma reaction chamber;

a light directing element that directs light emissions from along the different paths in the volume scanned by the scanner to the photosensitive detector, the photosensitive detector generating signals corresponding to detected amounts of the light from the volume from along the different paths, the signals representing the integral of the emission of the plasma from along the different paths; and a processor wherein the signals are analyzed and converted to data representative of one or more characteristics of the plasma along the different paths.

2. The apparatus as set forth in claim 1, wherein the photosensitive detector includes a photomultiplier tube and an associated high voltage power supply.

3. The apparatus as set forth in claim 1, wherein the photosensitive detector includes a photodiode.

4. The apparatus as set forth in claim 1, wherein the photosensitive detector includes a charge coupled device.

5. The apparatus as set forth in claim 1, wherein the photosensitive detector is in the form of an array of photosensitive detectors.

6. The apparatus as set forth in claim 5, wherein different ones of the photosensitive detectors detect different ranges of wavelengths of the light emissions from the volume scanned by the scanner, the different ones of the photosensitive detectors generating signals corresponding to detected amounts of the light from the volume at the different ranges of wavelengths.

7. The apparatus as set forth in claim 1, further comprising a wavelength selective element which prevents light emissions from the volume outside of a predetermined range of wavelengths from being detected by the photosensitive detector.

8. The apparatus as set forth in claim 7, wherein the wavelength selective element is an optical filter.

9. The apparatus as set forth in claim 7, wherein the wavelength selective element is a rotating filter wheel.

10. The apparatus as set forth in claim 7, wherein the wavelength selective element includes a spectrometer.

11. The apparatus as set forth in claim 1, wherein the light directing element includes an optical lens train.

12. The apparatus as set forth in claim 1, wherein the scanner includes a mirror that is turned about an axis.

13. The apparatus as set forth in claim 12, further comprising a motor for automatically turning the mirror.

14. The apparatus as set forth in claim 13, wherein the motor continuously rotates the mirror.

15. The apparatus as set forth in claim 1, wherein the processor converts the signals to data representative of plasma density.

16. A method for mapping characteristics at different locations in a volume of plasma in a plasma reaction chamber, comprising the steps of:

scanning a volume of plasma in a plasma reaction chamber to obtain light emission samples from along different paths in the volume of plasma;

directing light emissions from the scanned volume to a photosensitive detector;

generating signals corresponding to amounts of the light emissions detected by the photosensitive detector, the signals representing the integral of the emission of the plasma from along the different paths; and processing the signals to estimate density of the plasma from along the different paths.

17. The method as set forth in claim 16, further comprising the step of preventing light emissions outside of predetermined ranges of wavelengths from being detected by the photosensitive detector.

18. The method as set forth in claim 16, wherein the photosensitive detector includes an array of photosensitive detectors, different ones of the array of photosensitive detectors detecting different wavelengths of the light directed from the scanned volume, the generating step including generating one or more signals corresponding to an amount of light emissions at the different wavelengths detected by the different ones of the photosensitive detectors.

19. The method as set forth in claim 16, wherein the volume is scanned a plurality of times.

20. The method as set forth in claim 19, further comprising the step of preventing light emissions outside of a first predetermined range of wavelengths from being detected by the photosensitive detector during a first one or more scans of the volume and, subsequently, preventing light emissions outside of a second predetermined range of wavelengths from being detected by the photosensitive detector during a second one or more scans of the volume.

* * * * *